US011135193B2

(12) United States Patent
Oh et al.

(10) Patent No.: US 11,135,193 B2
(45) Date of Patent: *Oct. 5, 2021

(54) COMPOSITION CONTAINING MONOACETYLDIACYLGLYCEROL COMPOUND AS ACTIVE INGREDIENT FOR PREVENTING OR TREATING ASTHMA

(71) Applicants: Enzychem Lifesciences Corporation, Daejeon (KR); Korea Research Institute of Bio Science and Biotechnology, Daejeon (KR)

(72) Inventors: Sei-Ryang Oh, Daejeon (KR); Kyung Seop Ahn, Daejeon (KR); Su Ui Lee, Daejeon (KR); In Sik Shin, Daejeon (KR); Na-Rae Shin, Daejeon (KR); Tae-Suk Lee, Daejeon (KR); JongKoo Kang, Chungcheongbuk-do (KR); Young-Sik Jung, Seoul (KR); Yong-Hae Han, Seoul (KR); Ki Young Sohn, Seoul (KR)

(73) Assignee: Enzychem Lifesciences Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/127,930

(22) Filed: Sep. 11, 2018

(65) Prior Publication Data
US 2019/0008820 A1   Jan. 10, 2019

Related U.S. Application Data

(63) Continuation of application No. 14/912,920, filed as application No. PCT/KR2014/007663 on Aug. 19, 2014, now Pat. No. 10,098,864.

(30) Foreign Application Priority Data

Aug. 19, 2013 (KR) .......................... 10-2013-0098183

(51) Int. Cl.
| A61K 31/231 | (2006.01) |
| A61K 35/32 | (2015.01) |
| A23L 33/00 | (2016.01) |
| A23K 20/00 | (2016.01) |

(52) U.S. Cl.
CPC ............ *A61K 31/231* (2013.01); *A23K 20/00* (2016.05); *A23L 33/40* (2016.08); *A61K 35/32* (2013.01); *A23V 2002/00* (2013.01)

(58) Field of Classification Search
CPC .................................................. A61K 31/231
See application file for complete search history.

(56) References Cited

U.S. PATENT DOCUMENTS

| 7,662,853 B2 | 2/2010 | Kim |
| 7,868,196 B2 | 1/2011 | Lee et al. |
| 2008/0200543 A1 | 8/2008 | Kim |
| 2010/0010087 A1 | 1/2010 | Hong |
| 2010/0137435 A1 | 6/2010 | Kim |

FOREIGN PATENT DOCUMENTS

| CA | 2849289 A1 | 3/2013 |
| KR | 20000071887 A | 11/2000 |
| KR | 20050103259 A | 10/2005 |
| KR | 20060047447 A | 5/2006 |
| WO | 9926640 A1 | 6/1999 |
| WO | WO 99/26640 * | 6/1999 |
| WO | 2005/112912 A1 | 12/2005 |

OTHER PUBLICATIONS

International Preliminary Report on Patentability and Written Opinion of the International Searching Authority with English Language Translation, dated Dec. 17, 2014, Application No. PCT/KR2014/007663.

Shin, In-Sik, et al., "EC-18, a synthetic monoacetyldiglyceride (1-palmitoyl-2-linoleoyl-3-acetylglycerol), attenuates the asthmatic response in an aluminum hydroxide/ovalbumin-induced model of asthma", International Immunopharmacology, vol. 18, (2014), 116-123.

Letter/Written Disclosure of the Supplemental Information Disclosure Statement for the above-referenced application, filed herewith of Apr. 13, 2018, 2 pages.

Examination Report, dated Aug. 31, 2016, in connection with corresponding Australian Patent Application No. 2014309570, 3 pages.

Response, filed Mar. 2, 2017, to Examination Report, dated Aug. 31, 2016, in connection with corresponding Australian Patent Application No. 2014309570, 19 pages.

Notice of Acceptance, dated Apr. 6, 2017, in connection with corresponding Australian Patent Application No. 2014309570, 3 pages.

Response, filed Nov. 22, 2017, to Extended European Search Report, dated May 9, 2017, in connection with corresponding European Patent Application No. 14837475.4, 39 pages.

(Continued)

*Primary Examiner* — Sahar Javanmard
(74) *Attorney, Agent, or Firm* — Mintz Levin Cohn Ferris Glovsky and Popeo, P.C.; Peter F. Corless

(57) ABSTRACT

The present invention relates to a pharmaceutical composition containing a monoacetyldiacyiglycerol compound as an active ingredient for preventing or treating asthma, and a functional health food composition for preventing or treating asthma. The monoacetyldiacylglycerol compound of the present invention inhibits the expression of IL-4 in EL-4 cells, which are mouse T cell lymphoma cells, reduces hypersensitivity of airway in an asthma-induced animal model, and inhibits the infiltration of inflammatory cells into the bronchial tube. In addition, the compounds of the present invention inhibit the generation of IgE in the serum and bronchoalveolar lavage fluid, have an excellent effect of inhibiting the expression of Th2 cytokines (IL-4, IL-5, and IL-13) in the lung, thereby overcome side effects of the currently used therapeutic agents for asthma, have no toxicity, and exhibit a superior therapeutic effect, and thus can be useful as a composition for preventing, treating, and alleviating asthma.

14 Claims, 6 Drawing Sheets

(56) References Cited

OTHER PUBLICATIONS

Yang et al."Stimulatory Effects of Monoacetyldiglycerides on Hematopoiesis." Biological & Pharmaceutical Bulletin, Pharmaceutical society of Japan, vol. 27, No. 7 (Jul. 10, 2014), pp. 1121-1125.
Search Report in European Application No. 14837475.4 dated May 9, 2017.
Kuo et al., "Effect of the Velvet Antler of Formosan Sambar Deer (*Cervus unicolor swinhoei*) on the Prevention of an Allergic Airway Response in Mice," Evidence-Based Complementary and Alternative Medicine, 2012; 2012: 481318: pp. 1-10.

\* cited by examiner

[FIG. 1]
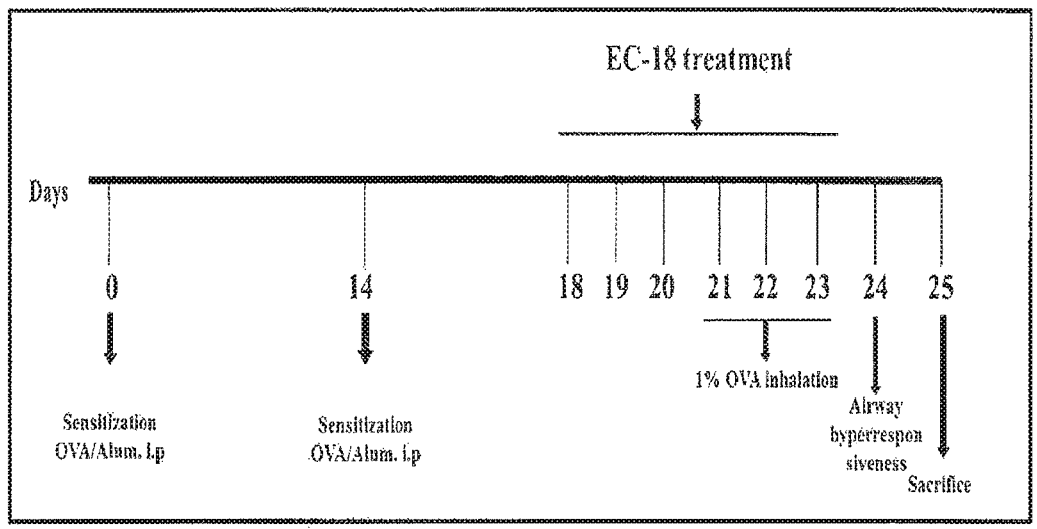
[FIG. 2]
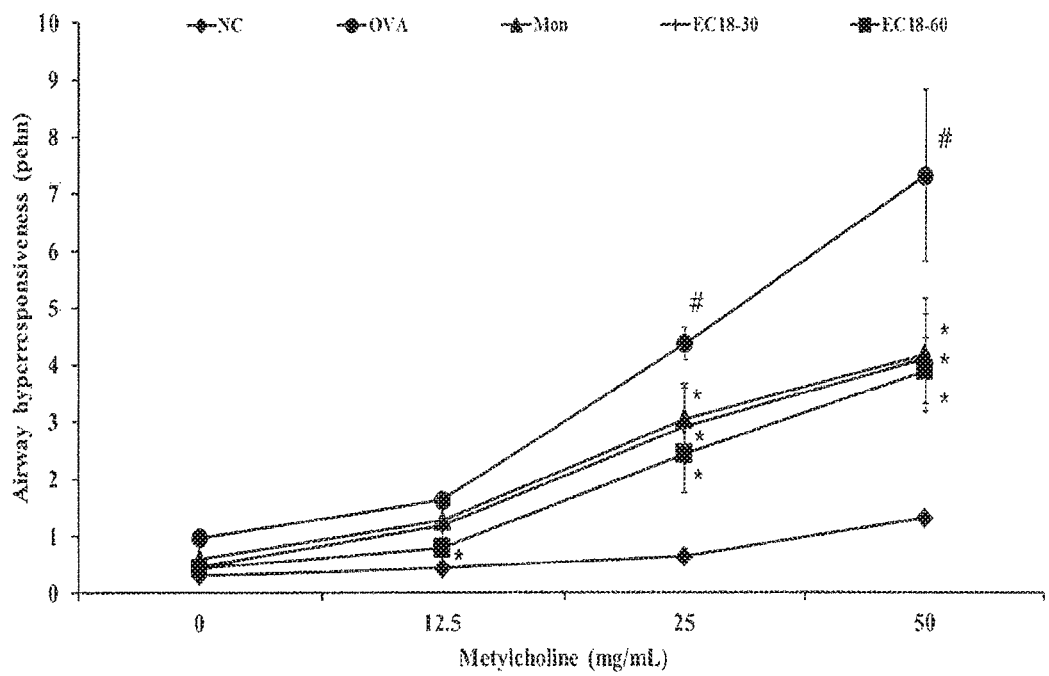

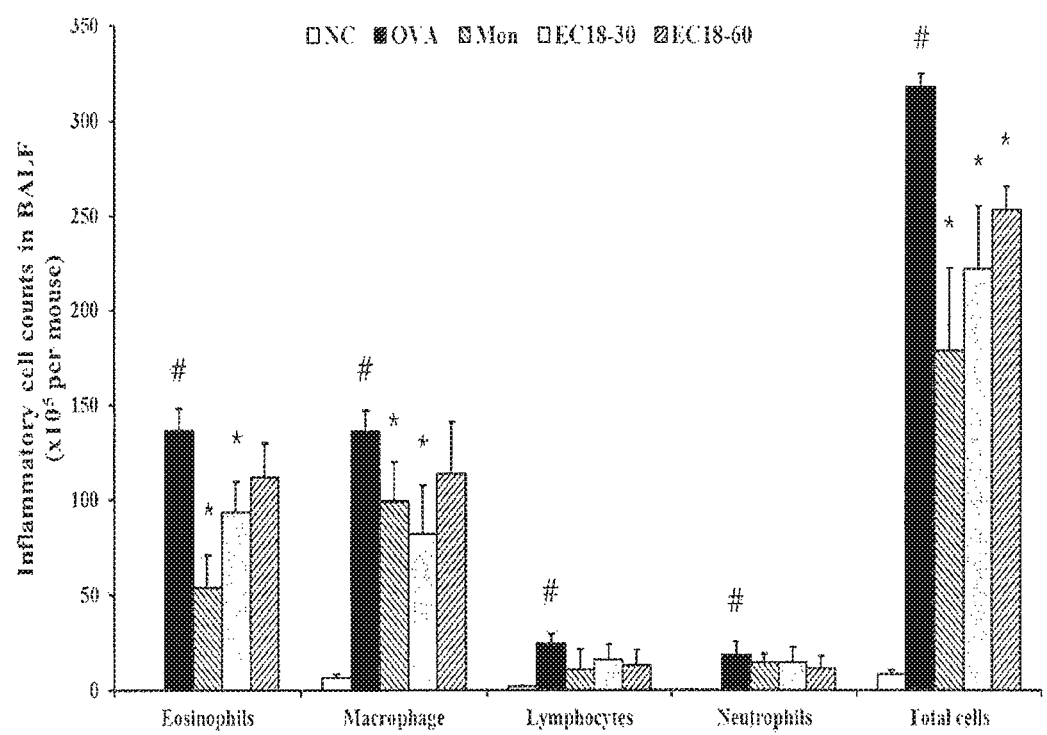
[FIG. 3]

[FIG. 4]
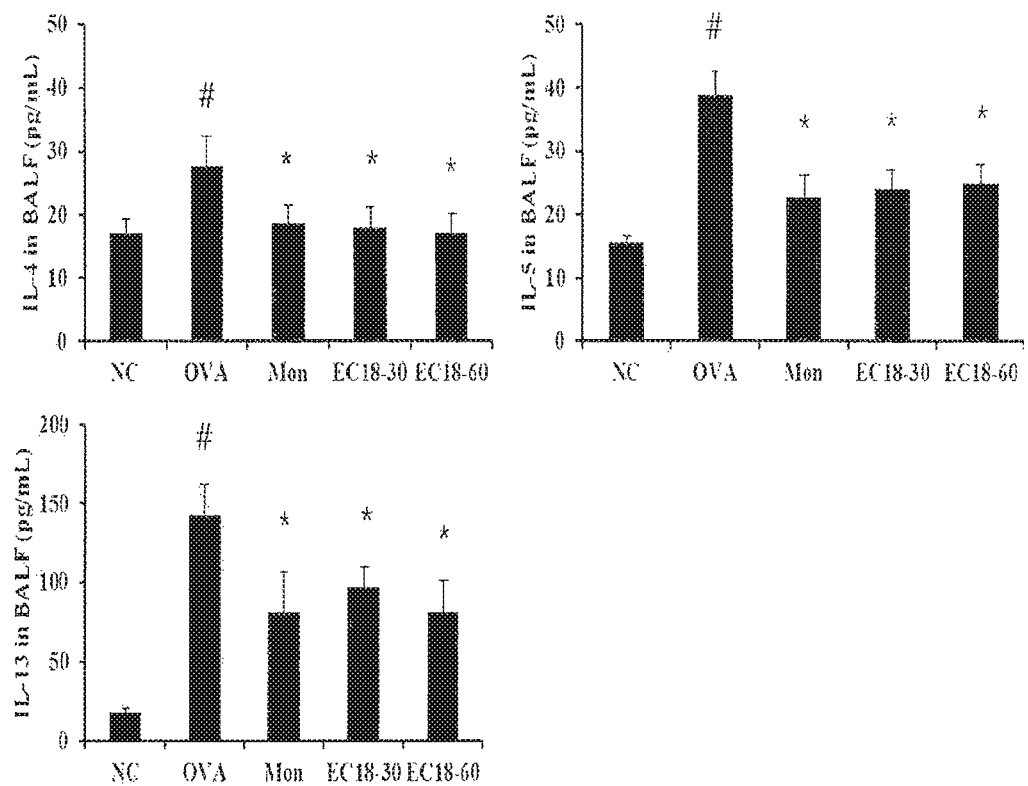

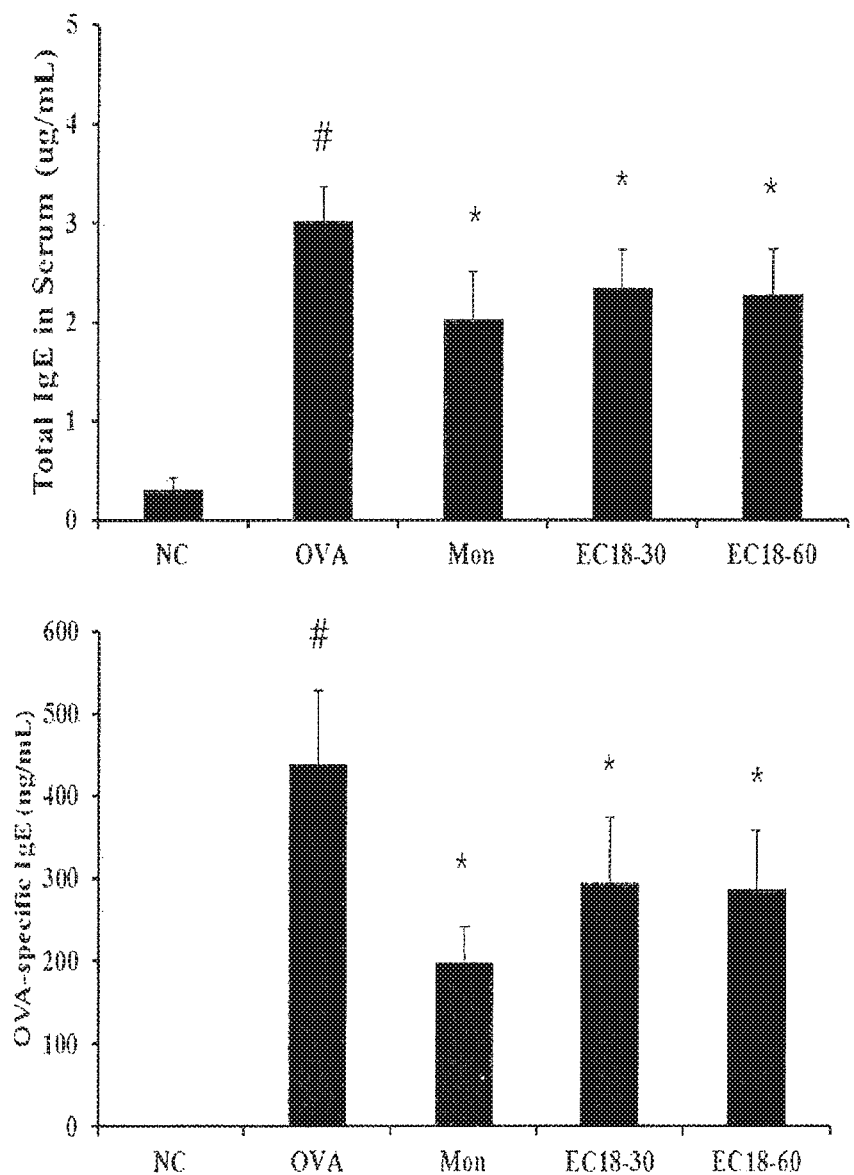
[FIG. 5]

[FIG. 6]
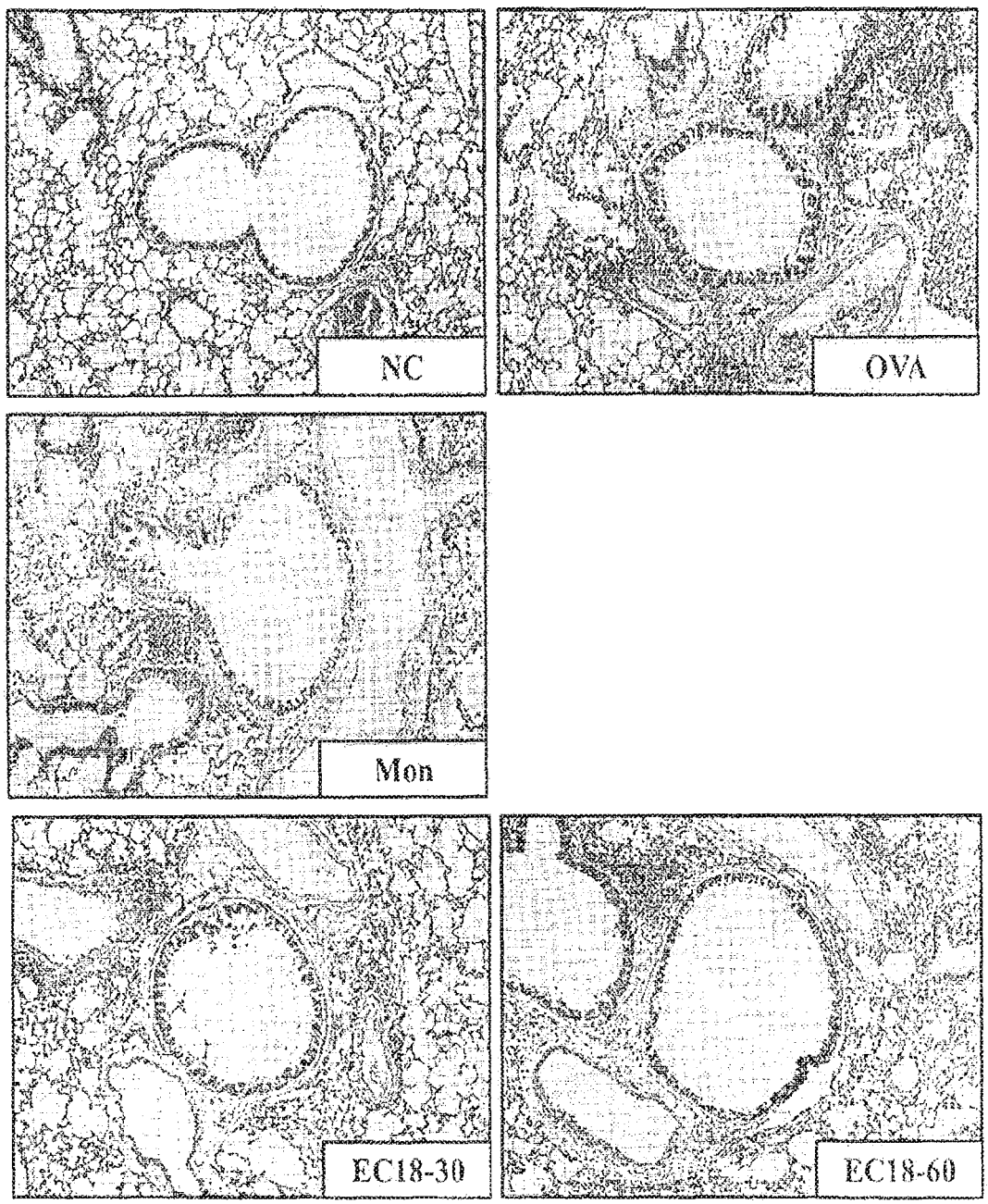

[FIG. 7]
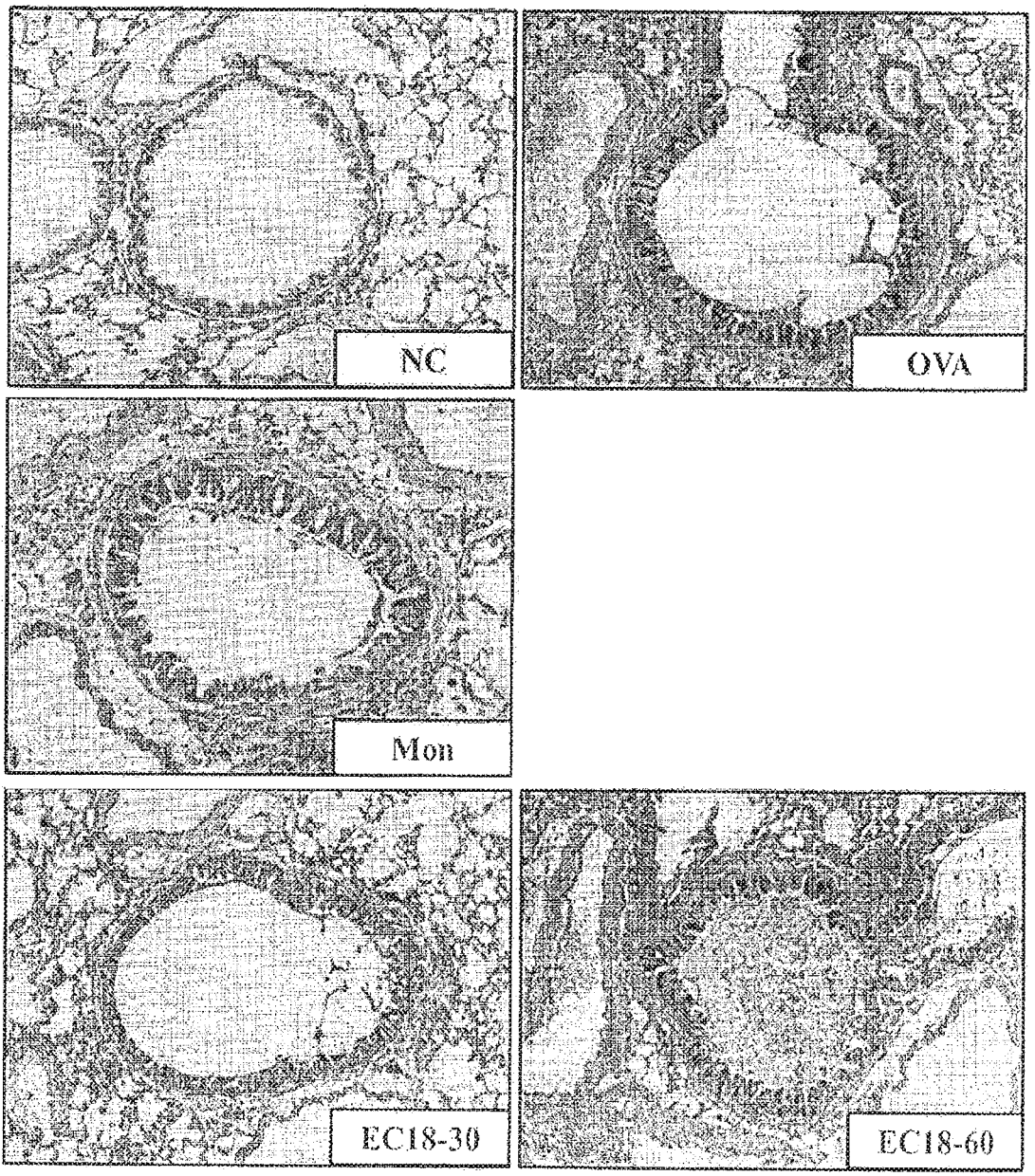

COMPOSITION CONTAINING MONOACETYLDIACYLGLYCEROL COMPOUND AS ACTIVE INGREDIENT FOR PREVENTING OR TREATING ASTHMA

RELATED APPLICATIONS

This application is continuation application to U.S. application Ser. No. 14/912,920, filed on Feb. 18, 2016, which is the U.S. national stage pursuant to 35 U.S.C. § 371, of International application Ser. No. PCT/KR2014/007663, filed Aug. 19, 2014, which are hereby expressly incorporated by reference in their entirety.

TECHNICAL FIELD

The present invention relates to a pharmaceutical composition for preventing or treating asthma, and a functional health food for preventing or alleviating asthma, which contain, as an active ingredient, a monoacetyldiacylglycerol compound.

BACKGROUND ART

With recent rapid industrial development, the life environment has been contaminated and eating habits have changed, and thus various allergic diseases increased. Particularly, the incidence of asthma among such allergic diseases has greatly increased. Asthma is a lung disease characterized by chronic inflammation of the airways and airway hyperresponsiveness, and is caused by air pollutants, yellow sand, allergens, etc. It is known that the prevalence of asthma is higher in children than in adults and is increasing due to changes in eating habits and the Westernization of eating habits. It is known that mechanisms of development of asthma are very diverse. In such mechanisms, T helper type 2 (Th2) type immune responses, and thus the secretion of interleukin-4, 5 and 13, etc., increases, and together with such responses, many inflammatory cells, including neutrophils, migrate and infiltrate into lung tissue. In addition, numerous inflammatory cells release a variety of proinflammatory factors and chemotactic factors, which make inflammatory responses worse, increase mucus secretion from goblet cells in the airways, and cause airway hyperresponsiveness. Due to such a series of responses, asthma patients show clinical symptoms, including difficulty in breathing, cyanosis, and chest pain.

Drugs that are currently used for the treatment of asthma include steroidal agents, bronchodilators or antibiotics. Steroidal agents and antibiotics are used to treat asthma by inhibition of immune responses and inflammatory responses, and bronchodilators are used to offset clinical symptoms such as difficulty in breathing. However, such drugs cause side effects such as immune suppression and bone marrow suppression, antibiotic resistance, and also cause side effects when they are used over a long period of time, and thus the use of such drugs as asthma therapeutic agents is very limited. Accordingly, there has been a need for the development of a natural material or a new compound, which overcomes such side effects, is less toxic, and has excellent therapeutic effects.

EC-18, as a kind of monoacetyldiglyceride compounds, was separated or extracted from the natural deer antler. EC-18 is known to be hematopoiesis. Also, it is known that EC-18 Increases survivability ratio of animals in sepsis animal model experiment using cecal-ligation-puncture, and shows no-toxicity in GLP (Good Laboratory Practice) toxicity test. However, the effect of monoacetyldiacylglycerol compounds including EC-18 is not known or disclosed in allergic asthma. Accordingly, the present inventors have made extensive efforts to develop an agent for treating asthma, which is derived from a natural material or is a new compound. As a result, the present inventors have found that a monoacetyldiacylglycerol compound reduces airway hyperresponsiveness and inhibits infiltration of inflammatory cells into bronchi, and thus can be effectively used for the prevention or treatment of asthma, thereby completing the present invention.

DISCLOSURE

Technical Problem

It is an object of the present invention to provide a pharmaceutical composition for preventing or treating asthma, and a functional health food for preventing or alleviating asthma, which contain, as an active ingredient, a monoacetyldiacylglycerol compound represented by the following formula 1.

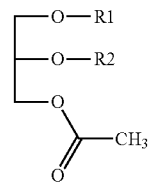

[Formula 1]

wherein R1 and R2 are independently a fatty acid residue of 14 to 22 carbon atoms.

Another object of the present invention is to provide a method for preventing or treating asthma, which comprises administering the pharmaceutical composition to a subject who is at risk of developing asthma or suffers from asthma.

Technical Solution

To achieve the above objects, in one aspect, the present invention provides a pharmaceutical composition for preventing or treating asthma, which contains, as an active ingredient, a monoacetyldiacylglycerol compound represented by the following formula 1.

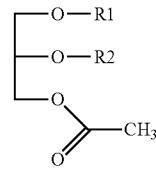

[Formula 1]

wherein R1 and R2 are independently a fatty acid group of 14 to 22 carbon atoms. In the Specification, the fatty acid group means the carboxyl group of fatty acids from which —OH group is extracted.

In detail, the pharmaceutical composition for preventing or treating asthma according to the present invention includes a monoacetyldiacylglycerol compound represented by the Formula 1. In the present Invention, the term "monoacetyl diacyl glycerol compound" means glycerol compounds having one acetyl group and two acyl groups, and can be referred as "monoacetyl diacyl glycerol (MADG)".

In the monoacetyl diacyl glycerol compound of Formula 1, R1 and R2 are independently a fatty acid residue of 14 to 22 carbon atoms. Preferably, non-limiting examples of R1 and R2 include palmitoyl, oleoyl, linoleoyl, linolenoyl, stearoyl, myristoyl, arachidonoyl, and so on. Preferable combinations of R1 and R2 (R1/R2) include oleoyl/palmitoyl, palmitoyl/oleoyl, palmitoyl/linoleoyl, palmitoyl/linolenoyl, palmitoyl/arachidonoyl, palmitoyl/stearoyl, palmitoyl/palmitoyl, oleoyl/stearoyl, linoleoyl/palmitoyl, linoleoyl/stearoyl, stearoyl/linoleoyl, stearoyl/oleoyl, myristoyl/linoleoyl, myristoyl/oleoyl, and so on. In optical activity, the monoacetyl diacyl glycerol compound of Formula 1 can be (R)-form, (S)-form or a racemic mixture.

In one embodiment, the monoacetyl diacyl glycerol compound is a compound of the following Formula 2.

[Formula 2]

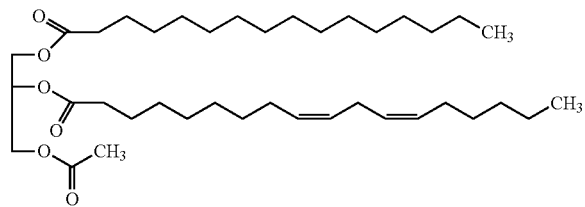

The compound of Formula 2 is 1-palmitoyl-2-linoleoyl-3-acetylglycerol, sometimes referred as "EC-18" in this specification. R1 and R2 of the compound of Formula 2 are palmitoyl and linoleoyl, respectively.

The monoacetyldiacylglycerol compounds can be separated and extracted from the natural deer antler or can be produced by known organic synthesis methods (Korean Registered Patents No. 10-0789323). More specifically, deer antler is extracted with hexane, followed by extracting the residue with chloroform and removing the chloroform to provide chloroform extracts. The volume of the solvents for this extraction is just enough to immerse the deer antler. In general, about 4-5 liters of hexane and/or chloroform for 1 kg of deer antler is used, but not limited thereto. The extracts obtained by this method is further fractionated and purified using series of silica gel column chromatograph and TLC method to obtain the monoacetyldiacyglycerol compound for the present invention. A solvent for the extraction is selected among chloroform/methanol, hexane/ethylacetate/acetic acid, but not limited thereto.

A chemical synthetic method for the preparation of monoacetyldiacylglycerol compounds is shown in Korean Registered Patents No. 10-0789323. Specifically, the method comprises (a) a step of preparing 1-R1-3-protecting group-glycerol by adding a protecting group in the position 3 of 1-R1-glycerol; (b) a step of preparing 1-R1-2-R2-3-protecting group-glycerol by introducing R2 in the position 2 of the 1-R1-3-protecting group-glycerol; and (c) a step of preparing the desired monoacetyldiacylglycerol compound by performing a deprotection reaction and the acetylation reaction of the 1-R1-3-protecting group-glycerol at the same time. The monoacetyldiacylglycerol compound may be further purified if necessary. Alternatively, monoacetyldiacylglycerol compounds can be prepared by acid decomposition of phosphatidylcholine (acetolysis) but is not limited thereto. Stereoisomers of the compounds of formula (I) are also within the scope of the invention.

It has been found in the present invention that the monoacetyldiacylglycerol compound can reduce the secretion of IgE or a cytokine selected from the group consisting of IL-4, IL-5 and IL-13, indicating that it can be effectively used for the prevention or treatment of asthma.

As used herein, the term "asthma" refers to a condition in which the bronchial tubes in the lungs become inflamed. It also means a disease in which the bronchial tubes are sometimes narrowed to show symptoms, including breathlessness, feeble breathing, and severe coughing. In addition, it refers to an allergic disease caused by the allergic inflammatory reaction of bronchi. Typical symptoms of asthma include shortness of breath, coughing, wheezing, etc., and symptom alleviators (bronchodilators) that alleviate narrowed bronchial tubes within a short time, or disease modulators (anti-inflammatory agents, leukotriene modulators) that prevent asthma attack by inhibiting allergic inflammation of the bronchial tubes, are typically used for the treatment of asthma. In the present invention, the asthma may be bronchial asthma, allergic asthma, atopic asthma, non-atopic asthma, exercise-induced asthma, cardiac asthma, or alveolar asthma, but is not limited thereto. As used herein, the term "preventing" refers to all actions that inhibit or delay the development of asthma by administering the composition, and the term "treating" refers to all actions that alleviate or beneficially change asthma by administering the composition.

It is known that interleukin-4 (IL-4), interleukin-5 (IL-5) and interleukin 13 (IL-13), which are cytokines produced by Th2 (helper T cell Type 2) cells, play as important mediators in bronchial asthma (Coyle A J. et al. 1995. Am J Respir Cell Mol Biol. 13(1): 54-9; Nakajima H. et al. 1992. Am. Rev. Respir. Dis. 146(2): 374-7; Wills-Karp, M. et al. 1998. Sci. 282(5397): 2258-61; Cohn et al., 2004; Medoff et al., 2008). Specifically, as is known in the art, an antigen that causes bronchial asthma is primarily removed by macrophages, and when the alveolar macrophages activated in this process stimulate B cells to produce IgE, the IgE activates mast cells to induce initial early asthmatic responses. In addition, B cells exposed to the asthma-inducing antigen stimulates CD4 T cells to differentiate into Th2 cells, and the differentiated Th2 cells promotes secretion of cytokines such as IL-4, IL-5 and IL-13 in lung tissue and bronchoalveolar lavage fluids. Bronchial hyperresponsiveness and airway obstruction are induced by these cytokines, causing asthmatic responses. Thus, asthmatic responses can be inhibited by inhibiting secretion of IgE or a cytokine selected from the group consisting of IL-4, IL-5 and IL-13.

In examples of the present invention, i) the inhibitory activities of monoacetyldiacylglycerol compounds against phorbol myristate acetate (PMA)-induced IL-4 expression in EL-4 cells that are mouse T lymphoma cells were measured, and as a result, it was found that a number of monoacetyldiacylglycerol compounds, including EC-18, showed significant inhibitory activities (Example 2), and ii) the productions of IL-4, IL-5 and IL-13 in the bronchoalveolar lavage fluid from asthma-induced animal models were measured, and as a result, it was shown that the productions of IL-4, IL-5 and IL-13 in the asthma-induced group all greatly increased compared to those in the normal control group, whereas the productions of these factors in the group administered with the monoacetyldiacylglycerol compound (EC-18) significantly decreased (Example 6 and FIG. 4), and iii) the secretions of serum IgE and ovalbumin-specific IgE were measured, and as a result, it was shown that the secretions of serum IgE and ovalbumin-specific IgE in the asthma-induced group all greatly increased compared to those in the normal control group, whereas serum IgE and ovalbumin-specific IgE in the group administered with the monoacetyldiacylglycerol compound (EC-18) significantly decreased (Example 7 and FIG. 5). This suggests that the monoacetyldiacylglycerol compound is effective for the treatment of asthma.

In addition, it has been found in the present invention that the monoacetyldiacylglycerol compound can reduce the number of inflammatory cells around bronchi or blood vessels or can reduce mucus secretion from goblet cells of the bronchial epithelium. Asthma patients were subjected to bronchoalveolar lavage and inflammation of the airways was examined, and as a result, it was found that lymphocytes, mast cells, eosinophils and activated macrophages in the bronchoalveolar lavage fluids increased. Thus, it is generally known that asthma is an airway inflammatory disease and that a variety of inflammatory cells are mostly activated to secrete various mediators to induce asthma, indicating that a decrease in inflammatory cells is associated with the treatment of asthma (Haley K J, et al., Am J Respir Crit Care Med, 1998; 158:565-72). Meanwhile, in asthma, in addition to airway narrowing and the infiltration of inflammatory cells into bronchi, goblet cells are formed to secrete mucus, and collagen deposition strikingly appears. Thus, an increase in mucus secretion of the bronchi is also known as a kind of asthma symptom.

In examples of the present invention, inflammation in lung tissue was observed by H&E (Hematoxylin & Eosin) staining, and mucus secretion in the bronchi was observed by PAS (periodic acid Schiff) staining. As a result, i) it was shown that extensive infiltration of inflammatory cells around the bronchi and blood vessels of the asthma-induced group was observed, whereas infiltration of inflammatory cells around the bronchi and blood vessels in all the groups administered with the monoacetyldiacylglycerol compound (EC-18) decreased (Example 8 and FIG. 6), and ii) it was observed that mucus secretion from goblet cells of the bronchial epithelium in the asthma-induced group increased, whereas secretion from goblet cells of the bronchial epithelium in all the groups administered with the monoacetyldiacylglycerol compound (EC-18) significantly decreased (Example 8 and FIG. 7). Such results also indicate that the monoacetyldiacylglycerol compound is effective for the treatment of asthma.

The pharmaceutical composition containing monoacetyldiacylglycerol compounds of the present invention may additionally include conventional pharmaceutically acceptable carriers, excipients, or diluents. The amount of monoacetyldiacylglycerol compounds in the pharmaceutical composition can be widely varied without specific limitation, and is specifically 0.0001 to 100.0 weight %, preferably 0.001 to 50 weight %, more preferably 0.01 to 20 weight % with respect to the total amount of the composition.

The pharmaceutical composition may be formulated into various forms for oral or non-oral administration, for example one selected from a group consisting of tablet, bolus, powder, granule, capsule such as hard or soft gelatin capsule, emulsion, suspension, syrup, emulsifiable concentrate, sterilized aqueous solution, non-aqueous solution, freeze-dried formulation, suppository, and so on. In formulating the composition, conventional excipients or diluents such as filler, bulking agent, binder, wetting agent, disintegrating agent, and surfactant can be used. The solid formulation for oral administration includes tablet, bolus, powder, granule, capsule and so on, and the solid formulation can be prepared by mixing one or more of the active components and at least one excipient such as starch, calcium carbonate, sucrose, lactose, gelatin, and so on. Besides the excipient, a lubricant such as Magnesium stearate and talc can also be used. The liquid formulation for oral administration includes emulsion, suspension, syrup, and so on, and may include conventional diluents such as water and liquid paraffin or may include various such as wetting agent, sweeting agent, flavoring agent, and preserving agent. The formulation for non-oral administration includes sterilized aqueous solution, non-aqueous solution, freeze-dried formulation, suppository, and so on, and solvent for such solution may include propylene glycol, polyethylene glycol, vegetable oil such as olive oil, and ester for syringe injection such as ethyl oleate. Base materials of the suppository may include witepsol, macrogol, tween 61, cacao butter, Laurin and glycerogelatine.

The composition of the present invention can be administered in a pharmaceutically effective amount. The term "pharmaceutically effective amount" Is used to refer to an amount which is sufficient to achieve a desired result in a medical treatment. The "pharmaceutically effective amount" can be determined in accordance with type, age and sex of a subject, severity and type of disease, activity of drug, sensitivity to drug, administration time, period and route, excretion rate, and other well known criteria in medical field. The composition of the present invention can be administered alone or with other medicines sequentially or simultaneously, or administered once or several times. Considering all the above factors, it is important to dose the amount that can achieve the maximum effect with the minimum amount with no side effects, which can be readily determined by those skilled in the art. The preferable amount of the composition of the present invention can be varied in accordance with the condition and weight of patient, severity of disease, formulation type of drug, administration route and period of drug. Appropriate total amount of administration per 1 day can be determined by a doctor of related medical filed, and generally 0.001 to 1000 mg/kg, preferably 0.05 to 200 mg/kg, more preferably 0.1 to 100 mg/kg once or several times by dividing in 1 day. The composition of the present invention can be administered to any subject which requires the suppression of blood cancer or cancer metastasis. For example, the composition of the present invention can be administered to not only human but also non-human animal (specifically mammals) such as monkey, dog, cat, rabbit, guinea pig, rat, mouse, cow, sheep, pig, goat, and so on. The composition of the present invention can be administered by conventional various methods, for example, by oral or rectum administration, or by intravenous, intramuscular, subcutaneous or cerebrovascular injection.

As other aspect of the present invention, the present invention provides a functional health food for preventing or alleviating asthma, comprising monoacetyldiacylglycerol compounds of Formula 1 as an active component(s),

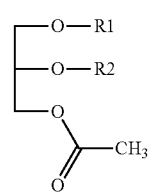

[Formula 1]

wherein R1 and R2 are independently a fatty acid group of 14 to 22 carbon atoms, but are not limited thereto.

In detail, the monoacetyldiacylglycerol compounds of the present invention can be included in the functional health food for preventing or alleviating asthma. The monoacetyldiacylglycerol compounds, asthma are previously explained in detail. The term "improving" means every change which reduces or advantageously changes the symptoms in a subject having or suspicious of having asthma.

When the composition of the present invention is included in the health functional food, the composition can be included alone or with other active component. The amount of the compounds of the present invention in the health functional food can be determined in accordance with the intended use of the health functional food. Generally, when preparing health functional food or beverage, the composition of the present invention can be included in the amount of less than 15 weight part, preferably less than 10 weight part. In case of long term administration for maintaining one's health, the amount of the composition can be reduced. However, since the active component does not cause any adverse effect, the amount of the composition can be increased by more than the above mentioned amount. The health functional food including the composition of the present invention can be any conventional food or beverage. Specific examples of the food include meat, sausage, bread, chocolate, candy, snack, biscuit, pizza, Ramen, noodles, gum, ice cream, dairy product, soup, beverage, tea, drink, alcoholic drink, vitamin complex, and so on. If necessary, the food of the present invention can also include food for an animal.

When the health functional food is beverage, the beverage may include conventional sweetener, flavoring agent, natural carbohydrate, and so on. Examples of the natural carbohydrate include monosaccharide such as glucose and fructose, disaccharide such as maltose and sucrose, polysaccharide such as dextrin and cyclodextrin, and sugar alcohol such as xylitol, sorbitol, and erythritol. The preferable amount of the natural carbohydrate can be about 0.01 to 0.04 g, more preferably about 0.02 to 0.03 g with respect to 100 m of the beverage of the present invention. Examples of the sweetener includes natural sweeteners such as Thaumatin and Stevia extract and artificial sweeteners such as saccharin and aspartame. The health functional food of the present invention may further include various nutritional supplement, vitamin, electrolyte, flavoring agent, coloring agent, pectic acid and its salt, alginic acid and its salt, organic add, protective colloid, thickener, pH adjuster, stabilizer, preservative, glycerin, alcohol, juice and so on.

As another aspect of the present invention, the present invention provides a method for preventing or treating asthma, comprising a step of administering the pharmaceutical composition to a subject who is suspicious of having asthma. The "subject who is suspicious of having asthma" includes not only an animal including human being which has asthma but also potentially has asthma. The subject who is suspicious of having asthma can be effectively treated by administering the pharmaceutical composition of the present invention. The term "administering" means introducing the pharmaceutical composition of the present invention into the subject who is suspicious of having asthma by any means. The administration route can be any route such as oral or non-oral route. The method for treating asthma comprises a step of administering an effective amount of a pharmaceutical composition comprising the monoacetyldiacylglycerol compounds of formula I or pharmaceutically acceptable salt thereof to a patient in need thereof. An appropriate total amount of administration per 1 day can be determined by a physician, and is generally about 0.001 to about 1000 mg/kg, preferably, about 0.05 to 200 mg/kg, more preferably about 0.1 to about 100 mg/kg. The total administration amount per day can be administered once a day or can be administered in divided doses multiple times daily. However, the specific therapeutically effective amount of the monoacetyldiacylglycerol administered to a particular patient can be varied depending on the type and degree of the response to be achieved in the treatment, the specific composition, including whether another agent is included in the composition, the patient's age, body weight, general health status, sex, diet, administration time, administration route, the ratio of composition, treatment period, other drugs used together in the treatment and a variety of factors well known in the medical field.

Effect of Invention

The monoacetyldiacylglycerol compounds according to the present invention inhibit the expression of IL-4 in EL-4 cells that are mouse T lymphoma cells, and these compounds reduce airway hyperresponsiveness in asthma-induced animal models and inhibit the infiltration of inflammatory cells into bronchi. In addition, the compounds according to the present invention have excellent effects of inhibiting the production of IgE in serum and bronchoalveolar lavage fluids and inhibiting the expression of Th2 cytokines (IL-4, IL-5 and IL-13) in the lungs, overcome the side effects of currently available agents for treating asthma, are not toxic, and have excellent therapeutic effects. Thus, these compounds can be effectively used for the prevention, treatment and alleviation of asthma.

BRIEF DESCRIPTION OF THE DRAWINGS

FIG. 1 schematically shows experimental procedures performed in the present invention.

FIG. 2 is a graph showing the effect of EC-18 against airway hyperresponsiveness. In FIG. 2, NC represents a normal control group; OVA represents an asthma-induced group; Mon represents a drug control group; and EC18-30 and EC18-60 represent sample-administered groups (administered with 30 mg/kg and 60 mg/kg of EC-18, respectively).

FIG. 3 is a graph showing the effect of EC-18 on the number of inflammatory cells in bronchoalveolar lavage fluids.

FIG. 4 is a set of graphs showing the effect of EC-18 on the secretion of cytokines in bronchoalveolar lavage fluids.

FIG. 5 is a set of graphs showing the effects of EC-18 on the secretion of serum total IgE and ovalbumin-specific IgE.

FIG. 6 is a set of images showing the effect of EC-18 against inflammatory responses in lung tissue.

FIG. 7 is a set of images showing the effect of EC-18 against mucus secretion in lung tissue.

DETAILED DESCRIPTION OF THE INVENTION

A more detailed description of the invention will be made by reference to the attached drawings. Hereinafter, the present invention will be described in further detail with reference to examples. It is to be understood, however, that these examples are for illustrative purposes and are not intended to limit the scope of the present invention.

Example 1: Evaluation of Cytotoxicity of Monoacetyldiacylglvcerol Compounds in EL-4 Cells EL-4 cells that are mouse T lymphoma cells were suspended in 10% fetal bovine serum-containing RPMI medium (Gibco) at a concentration of $5 \times 10^4$ cells/ml, and 100 μl of the cell suspension was seeded into each well of a 96-well plate and cultured for 12 hours. Next, the cell culture was treated with monoacetyldiacylglycerol (MADG) compounds at the concentrations shown in Table 1 below, and was then additionally cultured for 24 hours. Next, according to the instruction provided in a CCK-8 kit (Dojindo) capable of counting cells, 10 μl of CCK-8 solution was added to the kit and allowed to react for 30 minutes to 4 hours, and then the absorbance (OD) at 570 nm was measured. Cell viability was calculated using the following equation 1, and the results of the calculation are shown in Table 1 below. In equation 1, the negative control group indicates a cell culture treated with 0.2% DMSO. In Table 1 below, the following abbreviations were used: PLAG: 1-palmitoyl-2-linoleoyl-3-acetylglycerol; POAG: 1-palmitoyl-2-oleoyl-3-acetylglycerol; PSAG: 1-palmitoyl-2-stearoyl-3-acetylglycerol; PPAG: 1-palmitoyl-2-palmitoyl-3-acetylglycerol, OPAG: 1-oleoyl-2-palmitoyl-3-acetylglycerol; OSAG: 1-oleoyl-2-stearoyl-3-acetylglycerol; LPAG: 1-linoeoyl-2-palmitoyl-3-acetylglycerol; and LSAG: 1-linoeoyl-2-stearoyl-3-acetylglycerol.

Cell viability (%)=[(OD 570 nm value of MADC-treated group)/(OD 570 nm value of negative control group)]×100    Equation 1

TABLE 1

| Sample | Concentration (μg/ml) | EL-4 cell viability (%, mean ± SD) | Sample | Concentration (μg/ml) | EL-4 cell viability (%, mean ± SD) |
|---|---|---|---|---|---|
| Negative control group | 0 | 100.00 ± 0.58 | Negative control group | 0 | 100.00 ± 2.20 |
| PLAG (EC-18) | 5 | 101.94 ± 1.47 | PPAG | 5 | 106.28 ± 1.39 |
| Ec-18 | 10 | 97.54 ± 8.05 | | 10 | 105.84 ± 1.38 |
| | 20 | 91.82 ± 3.48 | | 20 | 96.59 ± 0.69 |
| | 50 | 92.67 ± 3.43 | OPAG | 5 | 98.04 ± 0.94 |
| | 100 | 95.29 ± 2.89 | | 10 | 98.91 ± 1.68 |
| | 200 | 99.74 ± 6.14 | | 20 | 99.56 ± 2.86 |
| POAG | 5 | 106.94 ± 2.69 | OSAG | 5 | 102.62 ± 2.18 |
| | 10 | 106:39 ±1.19 | | 10 | 100.98 ± 2.37 |
| | 20 | 98.90 ± 1.16 | | 20 | 100.22 ± 0.68 |
| PSAG | 5 | 98.46 ± 0.33 | LPAG | 5 | 99.67 ± 1.15 |
| | 10 | 100.66 ± 1.25 | | 10 | 98.91 ± 0.50 |
| | 20 | 103.30 ± 2.15 | | 20 | 99.13 ± 1.18 |
| | | | LSAG | 5 | 103.82 ± 1.80 |
| | | | | 10 | 101.85 ± 1.00 |
| | | | | 20 | 98.15 ± 1.82 |

As shown in Table 1 above, the cell viabilities of EL-4 cells at varying concentrations of the monoacetyldiacylglycerol (MADG) compounds were analyzed, and as a result, it was shown that EC-18 showed no cytotoxicity at a concentration of 200 μg/mL or less, and the other compounds showed no cytotoxicity at a concentration of 20 μg/mL or less.

Example 2: Inhibition of EL-4 mRNA Expression by Monoacetyldiacylglycerol Compounds Based on the results of Example 1, each of the monoacetyldiacylglycerol compounds was added to EL-4 cells at a concentration of 20 μg/mL, and the effect thereof on the inhibition of PMA-induced expression of IL-4 mRNA in the EL-4 cells was measured. Specifically, the expression level of IL-4 mRNA induced by PMA (1 ng/mL) was measured using real-time polymerase chain reaction (real-time PCR) and quantitative real time polymerase chain reaction (qPCR). For cell preparation, EL-4 cells were seeded into a 6-well plate at a concentration of $1 \times 10^6$ cells/well and cultured for 12 hours, after which the cells were treated with each of the monoacetyldiacylglycerol compounds at a concentration of 20 μg/mL for 1 hour and treated with PMA at a concentration of 1 ng/ml, followed by culture for 12 hours. Total RNA was extracted from the cells using Trizol B (Invitrogen, USA) and quantified, and then cDNA was synthesized from the total RNA using an Omniscript RT kit (Qiagen, GmbH, Hilden, Germany). The synthesized cDNA as a template was mixed with each of the IL-4 and GAPDH primers shown in Table 2 below and was subjected to PCR using a PCR mix (PCR Master Mix, Bioneer, Korea) under the following conditions: denaturation at 94° C. for 5 minutes; and then 30 cycles, each consisting of 30 sec at 95° C., 45 sec at 60° C., and 45 sec at 72° C.; followed by enzyme inactivation at 72° C. for 10 minutes. The results of measuring the percent inhibition of expression of IL-4 mRNA in EL-4 cells as described above are shown in Table 3 below. The designation of each of the samples shown in Table 3 below is as described with respect to Table 1 above.

TABLE 2

| Genes | Primers |
|---|---|
| IF-4 | Sense 5'- GAA TGT ACC AGG AGC CAT ATC -3' |
| | Anti-sense 5'- CTC AGT ACT ACG AGT AAT CCA -3' |
| GAPDH | Sense 5'- AAC TTT GGC ATT GTG GAA GG -3' |
| | Anti-sense 5'- ACA CAT TGG GGG TAG GAA CA -3' |

TABLE 3

| Sample | Concentration (μg/mL) | PMA (1 ng/mL) | Expression level of IL-4 mRNA (percentage relative to PMA-treated group) | Inhibition (%) |
|---|---|---|---|---|
| Negative control group | 0 | – | 72.13 ± 7.13 | — |
| PMA-treated group | 0 | + | 100.01 ± 5.91 | — |
| PLAG | 20 | + | 78.17 ± 6.26 | 21.83 |
| POAG | 20 | + | 75.47 ± 13.15 | 24.53 |
| PSAG | 20 | + | 70.49 ± 17.78 | 29.51 |
| PPAG | 20 | + | 48.62 ± 19.38 | 51.38 |
| OPAG | 20 | + | 58.58 ± 21.74 | 41.42 |
| OSAG | 20 | + | 55.84 ± 25.77 | 44.16 |
| LPAG | 20 | + | 61.11 ± 27.49 | 38.89 |
| LSAG | 20 | + | 41.62 ± 17.61 | 58.38 |

As shown in Table 3 above, the expression level of IL-4 in the PMA-treated group increased, and the monoacetyldiacylglycerol compounds inhibited the expression IL-4 by 20-50% compared to that in the PMA-treated group (100%).

Example 3: Ovalbumin-Induced Asthma Models and Sample Administration 6-week-old female SPF (specific pathogen-free) Balb/c mice (average weight: 20 g) were purchased from Samtako (Korea). The animals were sufficiently fed with solid feed (antibiotic-free, Samyang Feed Co.) and water until the start point of the experiment, and acclimated at a temperature of 22±2° C., a humidity of 55±15%, and a 12-hr light/12-hr dark cycle for 1 week, and then used in experiments. After 1 week of the acclimation period as described above, the mice were sensitized by intraperitoneal administration of a suspension of 2 mg of aluminum oxide (A8222, Sigma-Aldrich, MO, USA) and 20 μg of ovalbumin (A5503, Sigma-Aldrich) in 200 μl of phosphate buffered saline at two-week intervals. During a period from day 21 to day 23 after the first intraperitoneal administration of ovalbumin, 1% ovalbumin was inhaled into the mice for 30 minutes using an ultrasonic nebulizer (NE-U12, Omron Corp., Japan). At 24 hours after the last ovalbumin challenge, the airway hyperresponsiveness of the mice was measured, and after 48 hours, the mice were anesthetized by intraperitoneal administration of Pentobarbital (50 mg/kg, Entobal, Hanil, Korea). Then, blood was collected through the saphenous vein, and the mice were subjected to tracheostomy. Next, each of the mice was subjected to bronchoalveolar lavage with a total of 1.4 ml of PBS to collect an analytical sample. The mice were divided into: a normal control group (NC; a group not administered and inhaled with ovalbumin); an asthma-induced group (OVA; a group administered and inhaled with ovalbumin); a drug control group (Mon; a group administered with 30 mg/kg of montelukast+administered and inhaled with ovalbumin); and sample-administered groups (EC18-30 and EC18-60; groups administered with 30 mg/kg and 60 mg/kg of EC-18, respectively, + administered and inhaled with ovalbumin). The drug and the sample were administered orally during a period from day 18 to day 23 after the first ovalbumin challenge (FIG. 1). Seven mice were used per group.

Example 4: Measurement of Airway Hyperresponsiveness

To measure airway hyperresponsiveness that is one of the major features of asthma, one chamber plethysmography (All Medicus, Korea) was used. The degree of airway resistance was evaluated by measuring enhanced pause (Pehn). For measurement of Pehn, the basis value was measured in a normal breathing state, and then PBS was inhaled for 3 minutes using an ultrasonic nebulizer, after which the Pehn value was measured for 3 minutes. Next, methacholine (A2251, Sigma-Aldrich) was inhaled while the concentration thereof was gradually increased from 12 to 25 and 50 mg/ml and then the Pehn value was measured. The results of the measurement are shown in Table 4 below.

TABLE 4

| Group | Methacholine concentration (mg/mL) | | | |
|---|---|---|---|---|
| | 0 | 12.5 | 25 | 50 |
| NC | 0.308 ± 0.04 | 0.432 ± 0.03 | 0.639 ± 0.14 | 1.302 ± 0.10 |
| OVA | 0.965 ± 0.07# | 1.629 ± 0.14# | 4.37 ± 0.28# | 7.318 ± 1.51# |
| Mon | 0.590 ± 0.07* | 1.261 ± 0.29* | 3.046 ± 0.61* | 4.182 ± 0.99* |
| EC18-30 | 0.465 ± 0.08* | 1.179 ± 0.49* | 2.914 ± 0.67* | 4.098 ± 0.78* |
| EC18-60 | 0.436 ± 0.08* | 0.778 ± 0.15* | 2.436 ± 0.68* | 3.887 ± 0.59* |

As shown in FIG. 4 above, the Pehn value in the asthma-induced group greatly increased compared to that in the normal control group, and the Pehn value in the montelukast-administered group (drug control group) significantly decreased compared to that in the asthma-induced group. The airway hyperresponsiveness in all the groups administered with 30 mg/kg and 60 mg/kg of EC-18 significantly decreased compared to that in the asthma-induced group, and was similar to that in the montelukast-administered group (FIG. 2).

Example 5: Isolation of Bronchoalveolar Lavage Fluid (BALF) and Counting of Total Cells An increase in the number of eosinophils is one of the major features of asthma. Thus, in order to measure the number of eosinophils, the following experiment was performed. The bronchoalveolar lavage fluid from each mouse was collected immediately after collection, and the number of total cells (excluding dead cells) was calculated using a hemocytometer. Next, the cells were attached to a slide using Cytospin (Hanil, Korea), and then subjected to Diff-Quik staining (Sysmex, Switzerland), and eosinophils and other inflammatory cells were observed with a microscope. Next, the number of inflammatory cells in each sample was counted, and the results of the cell counting are shown in Table 5 below.

TABLE 5

| | Inflammatory cell number ($10^5$ per mouse) | | | | |
|---|---|---|---|---|---|
| Group | Eosinophils | Macrophages | Lymphocytes | Neutrophils | Total cells |
| NC | 0 ± 0.0 | 7 ± 1.7 | 2 ± 0.5 | 0 ± 0.0 | 9 ± 2.0 |
| OVA | 137 ± 11.4# | 136 ± 10.9# | 25 ± 5.0# | 19 ± 7.1# | 317 ± 7.0# |
| Mon | 54 ± 17.8* | 99 ± 21.4* | 11 ± 10.6 | 14 ± 5.2 | 179 ± 44.0* |
| EC18-30 | 93 ± 16.4* | 82 ± 25.5* | 16 ± 8.7 | 15 ± 8.4 | 221 ± 33.5* |
| EC18-60 | 112 ± 18.7* | 113 ± 27.4 | 13 ± 8.7 | 12 ± 6.7 | 253 ± 12.8* |

As shown in Table 5 above, the number of total inflammatory cells in the asthma-induced group greatly increased compared to that in the normal control group, and particularly, an increase in the number of eosinophils was characteristically observed. However, the groups administered with EC-18 showed a significant decrease in the number of total inflammatory cells together with a decrease in the number of eosinophils, compared to the asthma-induced group (FIG. 3).

Example 6: Analysis of Cytokines in Bronchoalveolar Lavage Fluid (BALF)

The production of interleukins (IL-4, IL-5 and IL-13) in the bronchoalveolar lavage fluid isolated from each mouse was measured using a commercially available enzyme-linked immunosorbent assay (ELISA) kit (R&D System, USA). The analysis of each cytokine was performed according to the manufacturer's instruction, and the absorbance at 450 nm was measured using an ELISA reader (Molecular Devices, USA). The results of the analysis are shown in Table 6 below.

TABLE 6

| | Th2 cytokines (pg/mL) | | |
|---|---|---|---|
| Group | IL-4 | IL-5 | IL-13 |
| NC | 17.19 ± 2.29 | 15.64 ± 1.12 | 18.53 ± 2.45 |
| OVA | 27.57 ± 4.93# | 38.97 ± 3.56# | 142.48 ± 19.75# |
| Mon | 18.69 ± 3.00* | 22.74 ± 3.59* | 81.42 ± 25.59* |
| EC18-30 | 17.89 ± 3.46* | 24.12 ± 3.07* | 97.27 ± 12.80* |
| EC18-60 | 17.09 ± 3.08* | 25.02 ± 2.91* | 81.10 ± 20.46* |

A shown in Table 6 above, the secretion of the Th2-type cytokine IL-4 in the asthma-induced group greatly increased compared to that in the normal control group, whereas the secretion of IL-4 in the montelukast-administered group significantly decreased compared to that in the asthma-induced group. Furthermore, the secretion of IL-4 in the EC-18-administered groups significantly decreased compared to that in the asthma-induced group. In addition, the secretion of IL-5 and IL-13 in the EC-18-administered groups significantly decreased compared to that in the asthma-induced group (FIG. 4).

Example 7: Measurement of Serum IqE and Ovalbumin-Specific IqE

The blood collected through the saphenous vein was incubated at room temperature for 30 minutes, and then centrifuged (3000 rpm, 15 min) to obtain serum. For measurement of serum IgE and ovalbumin-specific IgE, ELISA was used. IgE was measured using commercially available IgE (Biolegend Ins., USA). For measurement of ovalbumin-specific IgE, in a 96-well flat bottom ELISA plate, ovalbumin was dissolved in 0.1 M $NaHCO_3$ buffer (pH 8.3) at a concentration of 20 μg/mL and incubated at 4° C. for 16 hours. Next, PBS containing 1% bovine serum albumin (BSA) was added to suppress nonspecific reactions. The serum sample was diluted at 1:400, allowed to react at room temperature for 2 hours, and then washed with PBS containing 0.05% Tween 20. Horseradish peroxidase (HRP)-conjugated goat anti-rat IgG polyclonal A was diluted 4000-fold and allowed to react at room temperature for 1 hour, and then color development was performed using 3,3'5,5'-tetramethylbenzidine substrate. Next, the absorbance at 450 nm was measured, and the results of the measurement are shown in Table 7 below.

TABLE 7

| Group | IgE (μg/mL) | OVA specific IgE (μg/mL) |
|---|---|---|
| NC | 0.30 ± 0.13 | — |
| OVA | 3.03 ± 0.34# | 438.84 ± 90.75# |
| Mon | 2.03 ± 0.49* | 198.15 ± 42.65* |
| EC18-30 | 2.35 ± 0.38* | 295.36 ± 77.93* |
| EC18-60 | 2.27 ± 0.46* | 287.79 ± 69.53* |

As shown in Table 7 above, serum IgE in the asthma-induced group significantly increased compared to that in the normal control group, whereas serum IgE in the drug control group (montelukast-administered group) significantly decreased compared to that in the asthma-induced group. Furthermore, serum IgE in all the groups administered with EC-18 significantly decreased compared to that in the asthma-induced group, and was similar to that in the montelukast-administered group. In addition, ovalbumin-specitic IgE in the asthma-induced group greatly increased compared to that in the normal control group, whereas ovalbumin-specific IgE in all the groups administered with EC-18 significantly decreased compared to that in the asthma-induced group (FIG. 5).

Example 8: Histopathological Examination

The lung was isolated from each mouse, and then immediately, fixed in 10% formaldehyde solution, cut finely, washed with running water for 8 hours, embedded in epoxy, and then sectioned with a microtome. Next, Hematoxylin & Eosin staining was performed in order to observe inflammation in the lung tissue. In addition, because mucus secretion in the bronchi significantly increases when asthma was induced, periodic acid Schiff (PAS, IMEB Inc., USA) staining was performed in order to observe the mucus secretion. Pathological changes in the lung tissue were observed using an optical microscope.

(1) When inflammatory reactions in the lung tissue were examined, the extensive infiltration of inflammatory cells around the bronchi and blood vessels of the asthma-induced group was observed. However, in the montelukast-administered group, a decrease in the infiltration of Inflammatory cells was observed, and in all the groups administered with EC-18, a decrease in the infiltration of inflammatory cells around the bronchi and blood vessels was observed. This decrease was similar to that in the montelukast-administered group (FIG. 6).

(2) When mucus secretion in the bronchi was examined, an increase in mucus secretion from goblet cells of the bronchial epithelium in the asthma-induced group was observed. However, it was shown that mucus secretion in the montelukast-administered group decreased, and mucus secretion from goblet cells of the bronchial epithelium in all the groups administered with EC-18 significantly decreased (FIG. 7).

While the present invention has been described with reference to the particular illustrative embodiments, it will be understood by those skilled in the art to which the present invention pertains that the present invention may be embodied in other specific forms without departing from the technical spirit or essential characteristics of the present invention. Therefore, the embodiments described above are considered to be illustrative in all respects and not restrictive. Furthermore, the scope of the present invention should be defined by the appended claims rather than the detailed description, and it should be understood that all modifications or variations derived from the meanings and scope of the present Invention and equivalents thereof are included in the scope of the present invention.

The invention claimed is:

1. A method for treating asthma, comprising:
administering to a subject suffering from or susceptible to asthma an effective amount of a compound of the following Formula (I):

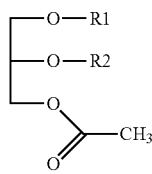

[Formula I]

wherein R1 and R2 are independently selected from the group consisting of palmitoyl, oleoyl, linoleoyl, linolenoyl, stearoyl, myristoyl, and arachidonoy.

2. The method of claim 1, wherein an effective amount of a compound of the following Formula 2 is administered to the subject:

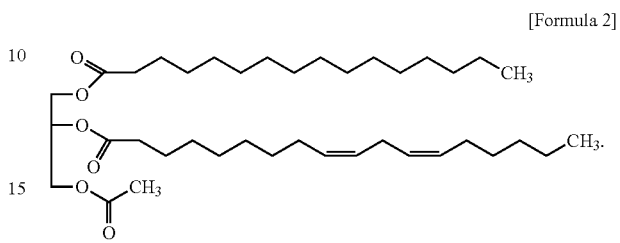

[Formula 2]

3. The method of claim 1 wherein the subject is suffering from bronchial asthma, allergic asthma, atopic asthma, non-atopic asthma, exercise-induced asthma, cardiac asthma or alveolar asthma.

4. The method of claim 1 wherein the compound of Formula 1 reduces the secretion of cytokine selected from the group consisting of IL-4, IL-5 and IL-13.

5. The method of claim 1 wherein the compound of Formula 1 reduces the secretion of IgE.

6. The method of claim 1 wherein the compound of Formula 1 reduces the inflammatory cells around the bronchi or vessels or reduces the mucus secretion of goblet cells of the bronchial epithelium.

7. The method of claim 1 wherein R1 and R2 (R1/R2) is selected from the group consisting of oleoyl/palmitoyl, palmitoyl/oleoyl, palmitoyl/linoleoyl, palmitoyl/linolenoyl, palmitoyl/arachidonoyl, palmitoyl/stearoyl, palmitoyl/palmitoyl, oleoyl/stearoyl, linoleoyl/palmitoyl, linoleoyl/stearoyl, stearoyl/linoleoyl, stearoyl/oleoyl, myristoyl/linoleoyl, myristoyl/oleoyl.

8. The method of claim 2 wherein the subject is suffering from bronchial asthma.

9. The method of claim 2 wherein the subject is suffering from allergic asthma.

10. The method of claim 2 wherein the subject is suffering from atopic asthma.

11. The method of claim 2 wherein the subject is suffering from non-atopic asthma.

12. The method of claim 2 wherein the subject is suffering from exercise-induced asthma.

13. The method of claim 2 wherein the subject is suffering from cardiac asthma.

14. The method of claim 2 wherein the subject is suffering from alveolar asthma.

* * * * *